United States Patent [19]

Spiegel et al.

[11] Patent Number: 4,481,206

[45] Date of Patent: Nov. 6, 1984

[54] SPIRO SUCCINIMIDE DERIVATIVE IN THE TREATMENT OF DEMENTIA OF THE ALZHEIMER TYPE

[75] Inventors: René Spiegel, Basel; Hans Weidmann, Binningen, both of Switzerland

[73] Assignee: Sandoz Ltd., Basel, Switzerland

[21] Appl. No.: 505,717

[22] Filed: Jun. 20, 1983

[30] Foreign Application Priority Data

Jun. 25, 1982 [GB] United Kingdom ............... 8218424

[51] Int. Cl.$^3$ ........................................... A61K 31/445
[52] U.S. Cl. .................................................. 424/267
[58] Field of Search ........................................ 424/267

[56] References Cited

U.S. PATENT DOCUMENTS 3,056,796 10/1962 Jucker et al. ..................... 260/294

OTHER PUBLICATIONS

Bubb et al., Proxis 55, 40, pp. 1144–1146 (1966).
Herz et al., Abstract, Arch. Exp. Pathol. Pharmacol. 253, No. 1, 46–47 (1966).
Costall et al., Neuropharmacology 13, No. 5, 353 (1974)–abstract.
Costall et al., J. Pharm. Pharmacol. 27, No. 4, 273 (1975)–abstract.
Costall et al., Psychopharmacologia 43, No. 1, 69 (1975)–abstract.
Kaakkola et al., Psychopharmacology 52, No. 1, 7 (1977)–abstract.
Perry, Alzheimer's Disease: Early Recognition of Potentially Reversible Deficits, 27, Ed. Glen & Whally, Churchill Livingstone: Edinburgh 1979.
Glen, Alzheimer's Disease, supra, p. 140.
Smart, Alzheimer's Disease, supra, p. 183.
Davis et al., Life Sciences 23, 1729 (1978).
Davies et al., Brain Research 138, 385 (1978).

*Primary Examiner*—Stanley J. Friedman
*Attorney, Agent, or Firm*—Gerald D. Sharkin; Robert S. Honor

[57] ABSTRACT

Spiro-(N'-methyl-piperidyl-4')-N-ethyl-succinimide for the treatment of Alzheimer's disease and senile dementia of the Alzheimer type.

3 Claims, No Drawings

SPIRO SUCCINIMIDE DERIVATIVE IN THE TREATMENT OF DEMENTIA OF THE ALZHEIMER TYPE

The present invention relates to a novel method for the treatment of presenile and senile dementia, also known as Alzheimer's disease (AD) and senile dementia of the Alzheimer type (SDAT).

Alzheimer's disease (AD) and SDAT are one of the most common causes of mental deterioration in the elderly. These brain diseases, which are pathologically and clinically very closely related, produce a progressive deterioration of cognitive functions, affect and behaviour, leading to the clinical syndrome of dementia.

Many of the symptoms of AD and SDAT, particularly the cognitive disturbances, have been attributed to a reduction of central acetylcholine neurotransmission. Many unsuccessful attempts have been made to treat the symptoms of AD and SDAT with drugs which interact with acetylcholine neurotransmission, such as blockers of acetylcholinesterase, e.g. physostigmine and acetylcholine precursors, e.g. choline. Another approach proposed is to treat patients with a centrally acting muscarinic cholinomimetic agent. Clinical trials so far published have not shown any significant effect on AD or SDAT and often the drug is not well tolerated.

Spiro-(N'-methyl-piperidyl-4')-N-ethyl-succinimide (hereafter the compound) is a known parasympathicomimetic substance with cholinomimetic, analgesic and sedating properties in animals. Subsequently only an isolated clinical trial with the compound has been published. W. Ph. Bubb and M. L. Hefti, Praxis 55 (40) 1144–1146 (1966) reported on the results of a pilot observation on 129 patients with functional gastric disturbances.

However, its use in the treatment of AD and SDAT has not been previously suggested. Indeed the compound was not before known to be a centrally active muscarinic agonist.

In accordance with the present invention it has now surprisingly been found that the compound is of use for the treatment of AD and SDAT.

The safety of the compound and its efficacy in the treatment of AD and SDAT was established in several clinical trials with healthy volunteers and patients suffering from clinically diagnosed AD and SDAT.

The reaction of the patients suffering from AD and SDAT in cognition and vigilance tests were compared with those of control groups. After a single dose of 1.0 mg p.o. or s.c. there was a tendency towards improved word and picture recognition. After repeated oral administration of up to 4 mg/day during approx. 10 weeks, significant improvements in cognitive functions such as orientation and memory could be achieved.

The compound was generally well tolerated by the patients and the healthy volunteers. Oral doses of up to 1.5–2.0 mg caused no or only very mild side effects. Doses of 2.0–3.0 mg were in some cases associated with qualitatively and quantitatively tolerable peripheral effects, typical of cholinomimetic compounds, such as hypersalivation, flushing, sweating and nausea. Gastrointestinal disorders occurred with one patient after 4.0 mg.

The present invention therefore provides a method for the treatment of dementia of the Alzheimer type which comprises administering a therapeutically effective amount of the compound or a pharmaceutically acceptable acid addition salt thereof to a subject in need of such treatment.

For this use, the dosage used will naturally depend on the mode of administration used and treatment desired. However, in general, satisfactory results are obtained when administered at a daily dosage of from about 0.5 to about 10 mg, and dosage forms suitable for oral administration comprise from about 0.1 mg to about 10 mg of the compound admixed with a solid or liquid pharmaceutical carrier or diluent.

Preferably the compound is administered at a daily dose of from 1.5 to 4 mg.

The compound may be administered in free base form or pharmaceutically acceptable salt form, e.g. the hydrochlorid form. Such salt forms exhibit the same order of activity as the free base form, and may be made in conventional manner.

Conveniently the compound is administered in the form of a pharmaceutical composition comprising the compound in free base form or in pharmaceutically acceptable acid addition salt form in association with a pharmaceutical carrier or diluent. The known pharmaceutical compositions are suitable and may be made by conventional techniques to be in the form of capsules, tablets, suppositories, dispersible powders, syrups, elixirs, suspensions or solutions as appropriate for enteral or parenteral administration. Preferably unit dosage forms are used. The compositions may contain conventional pharmaceutical excipients, e.g. diluents and carriers, such as water, alcohols, natural or hardened oil and waxes, calcium and sodium carbonate, calcium phosphate, kaolin, talc and lactose. Other excipients which may be used include suspending agents, lubricating agents, disintegrating agents, etc.

Compositions in tablet form may be coated by conventional techniques to delay disintegration of the tablet and/or absorption of the active ingredient in the gastrointestinal tract and thereby provide sustained action over a long period.

The compound may also be administered in the form of a pharmaceutical composition containing additionally a peripheral cholinergic blocker. Such blockers are known and include methylscopolamine, methylatropine and tropenzilium [Pakrol(R)].

In a further aspect the present invention provides a pack or dispenser device containing the compound for use in the treatment of AD and SDAT. The pack or dispenser device may contain for example a plurality of unit dosage forms containing the substance. These may be packed in metal or plastic foil, e.g. as in a blister pack. The pack or dispenser device may be together with instructions for administration of the compound.

The following is illustrative of suitable compositions for administration of the compound for the treatment of AD or SDAT.

1. Capsules

| Ingredient | Weight (mg) |
| --- | --- |
| Spiro-(N'—methyl-piperidyl-4')-N—ethyl-succinimide bromhydrate* | 1.385 |
| Lactose (200 mesh/inch) | 133.165 |
| Corn starch | 92 |
| Silicium dioxide (Aerosil 200) | 1.15 |
| Magnesium stearate | 2.3 |
| Total | 230 |

*corresponds to 1 mg base

The ingredients are compounded in conventional manner and filled into a 62 mg capsule.

2. Ampoules

| Ingredient | Weight/vol. (mg/ml) |
| --- | --- |
| Spiro-(N'—methyl-piperidyl-4')-N—ethyl-succinimide bromhydrate* | 13.85 |
| Sodium chloride | 8 |
| Water for injectable solutions | up to 1 ml |

*corresponds to 10 mg base

Ampoules are filled with 1 ml of the solution, sealed and sterilized at 121° C. for 15 minutes.

What we claim is:

1. A method for the treatment of Alzheimer's disease and dementia of the Alzheimer type which comprises administering to a subject in need of such treatment a therapeutically effective amount of spiro-(N'-methyl-piperidyl-4')-N-ethyl-succinimide or a pharmaceutically acceptable acid addition salt thereof admixed with a pharmaceutical carrier or diluent.

2. A method according to claim 1 wherein the active agent is administered at a daily dosage of from about 0.5 to about 10 mg.

3. A method according to claim 1 wherein the active agent is administered at a daily dosage of from about 1.5 to about 4 mg.

* * * * *